United States Patent [19]

Mullane

[11] Patent Number: 5,628,740
[45] Date of Patent: May 13, 1997

[54] ARTICULATING TOGGLE BOLT BONE SCREW

[76] Inventor: Thomas S. Mullane, 2308 SW. 4th Ave., Ft. Lauderdale, Fla. 33315

[21] Appl. No.: 497,178

[22] Filed: Jun. 30, 1995

Related U.S. Application Data

[63] Continuation of Ser. No. 173,619, Dec. 23, 1995, abandoned.

[51] Int. Cl.⁶ .................. A61F 5/00; A61B 17/56
[52] U.S. Cl. ............. 606/61; 606/61; 606/72; 623/17
[58] Field of Search ............ 606/60, 61, 62, 606/65, 72, 73; 623/17

[56] References Cited

U.S. PATENT DOCUMENTS

| | | | |
|---|---|---|---|
| 4,723,541 | 2/1988 | Reese . | |
| 4,827,918 | 5/1989 | Olerud . | |
| 4,836,196 | 6/1989 | Park et al. | 128/92 |
| 4,854,304 | 8/1989 | Zielke | 128/69 |
| 4,887,595 | 12/1989 | Heinig et al. | 606/61 |
| 4,887,596 | 12/1989 | Sherman | 606/61 |
| 4,946,458 | 8/1990 | Harms | 606/61 |
| 5,002,542 | 3/1991 | Frigg | 606/61 |
| 5,047,029 | 9/1991 | Aebi | 606/61 X |
| 5,057,109 | 10/1991 | Olerud | 606/61 |
| 5,129,900 | 7/1992 | Asher et al. | 606/61 |
| 5,133,717 | 7/1992 | Chopin | 606/61 |
| 5,196,014 | 3/1993 | Lin | 606/60 |
| 5,282,862 | 2/1994 | Baker | 606/61 |
| 5,306,275 | 4/1994 | Bryan | 606/72 |
| 5,312,404 | 5/1994 | Asher | 606/72 |

*Primary Examiner*—Sam Rimell
*Assistant Examiner*—Benjamin K. Koo
*Attorney, Agent, or Firm*—McHale & Slavin

[57] ABSTRACT

An articulation toggle bolt bone screw for use in surgical implants having particular usefulness in the stabilization of the human spine by fixation of vertebra. The apparatus employs a self-tapping anchoring screw having a ball joint socket for receipt of a rotatable threaded bolt. The ball joint allows angular placement of the bolt which is secured into position by an attachment nut coupling directly to the anchoring screw. An upper surface of the attaching nut is rounded allowing engagement of component devices. A rod clamp is disclosed for use in combination with the device providing attachment to support rods and serving to bias the bolt into a permanent fixed position upon attachment. An alternative embodiment is disclosed of the rod clamp providing a single support rod attachment system.

13 Claims, 3 Drawing Sheets

ARTICULATING TOGGLE BOLT BONE SCREW

This application is a continuation of Ser. No. 08/173,619 filed Dec. 23, 1993, now abandoned.

BACKGROUND OF THE INVENTION

1. Field of the Invention

This invention relates generally to threaded anchoring bolts and, more particularly to bone screws used in stabilization of human vertebrae.

2. Background of the Invention

The use of fixation devices for the treatment of vertebrae injuries and deformities is well known in the art. Various fixation devices correct curvatures, treat trauma, amend deformities, and remedy various degenerative spinal conditions. Implants typically consist of strategically placed screws used to anchor various component pieces such as support rods, crosslinks, caudal facing hooks, cranial facing hooks and the like components all of which form a spinal implant system.

Common to spinal implant systems is the necessity for proper anchoring to the bone so as to provide support for the aforementioned components. While bone screws are commonly used for anchoring, they are limited in their positioning due to the design of component pieces. Numerous patents are directed to component design in order to accommodate the bone screw, yet few patents are directed to bone screws that will accommodate existing component design. In many instances the combination of existing component design and bone screw design inhibits application to a particular spinal injury. For example, bone structure of the sacrum is typically soft, and often osteoporotic in the elderly. Perpendicular placement of a bone screw therein may not be possible and placement at an angle thereto may cause undue stress further affecting adjoining bones. Thus, if a common bone screw is employed, the component connector will be of special design.

For this and other reasons, screws located in bone structure typically use a specially designed clamp to attach to a component such as an alignment rod. A problem with specially designed clamps is that bone structure cannot be determined until the patient's bone is exposed causing the necessity of a large inventory of various sized clamps to be on hand during surgery, of which the surgeon must search to find the right combination. Even if a clamp combination is predicted, insertion of the screw may still require angular insertion due to muscle or tender nerve locations. The result is a bone screw which exerts unpredictable forces upon attachment to component connectors. Further, any movement of muscle and other tissue increases the difficulty of the operation and can be a major trauma to a person.

A conventional bone screw consists of a single shaft with a coarse thread at one end for threading into the bone and a machine thread at the other end for coupling to components. Another type of bone screw has a U-shaped top which acts as a saddle for attachment to an alignment rod. If the screw is placed incorrectly for any reason, the rod clamp must be made to accommodate the position.

A number of patents exist which demonstrate the reliance on the saddle type screw support and various designs to accommodate the problem. U.S. Pat. No. 5,133,717 sets forth a sacral screw with a saddle support. Disclosed is the use of an auxiliary angled screw to provide the necessary support in placing the screw in an angular position for improved anchoring.

U.S. Pat. No. 5,129,900 sets forth an attachment screw and connector member that is adjustably fastened to an alignment rod. An oblong area provided within each connector member allows minute displacement of the alignment rod.

U.S. Pat. No. 5,129,900 discloses an apparatus which utilizes a screw having a lower portion adapted for insertion into the bone and a second portion of the screw including a means for adjusting vertical placement of an alignment rod.

U.S. Pat. No. 4,887,595 discloses a screw that has a first externally threaded portion for engagement with the bone and a second externally threaded portion for engagement with a locking nut. The disclosure illustrates the use of a singular fixed shaft.

U.S. Pat. No. 4,946,458 discloses a screw which employs a spherical portion which is adapted to receive a locking pin so as to allow one portion of the screw to rotate around the spherical portion. A problem with the screw is the need for the locking pin and the inability of the base screw to accommodate a threaded extension bolt.

U.S. Pat. No. 5,002,542 discloses a screw clamp wherein two horizontally disposed sections are adapted to receive the head of a pedicle screw for use in combination with a hook which holds a support rod at an adjustable distance.

U.S. Pat. No. 4,854,304 discloses the use of a screw with a top portion that is adaptable for use with a specially designed alignment rod to permit compression as well as distraction.

U.S. Pat. No. 4,887,596 discloses a pedicle screw for use in coupling an alignment rod to the spine wherein the screw includes a clamp permitting adjustment of the angle between the alignment rod and the screw.

U.S. Pat. No. 4,836,196 discloses a screw with an upper portion design for threadingly engaging a semi-spherical cup for use with a specially designed alignment rod. The alignment rod having spaced apart covertures for receipt of a spherical disc allowing a support rod to be placed at angular positions.

Therefore, what is lacking in the art is an articulated toggle bolt having a screw base for anchoring into bone and a means for top loading of spinal implant components.

SUMMARY OF THE INVENTION

The instant invention is directed to an articulating toggle bolt bone screw having particular usefulness with a clamping mechanism for anchoring aligning rods used in a vertebra fixation system. The apparatus consists of a rigid shank having a self-taping coarse thread formed along a length of the shank for attachment to bone and a spherical shaped socket disposed at the opposite end. A toggle bolt attaches to the shank by use of a ball shaped end that fits within the socket. An attachment cap having a centrally disposed aperture and rounded top threadingly engages the socket portion of the anchoring screw to secure the ball shaped end to the socket. The aperture allows toggle bolt articulation providing the surgeon with the ability to attach the screw to bone structure and place the toggle bolt in a precise position for subsequent attachment to component pieces.

Once the screw is anchored into the bone an alignment rod can be coupled to the toggle bolt by use of a rod clamp which is formed from a bifurcated compressible sleeve. The clamp has an aperture for insertion of the bolt and a perpendicularly disposed opening for placement of the alignment rod. A lower portion of the clamp includes a rounded surface that corresponds to a rounded surface of the attachment cap.

In operation the screw is threaded into bone structure of a patient. The rod clamp is attached to the alignment rod and positioned onto the toggle bolt. The toggle bolt is then moved into a position so as to avoid stress on components which could force associated bones into improper positioning. A nut is used to fasten the clamp to the screw wherein the compression causes the toggle bolt to fictionally engage the attachment cap for permanent positioning of the toggle bolt and alignment rod.

Accordingly, an objective of the instant invention is to provide a top-loading bone screw which provides an adjustable range of motion for subsequent attachment of components.

Still another objective is to provide a screw that can be placed in an angular position and permanently fixed in said position.

Yet still another objective is to provide a rod clamp for use in combination with the bone screw of the instant invention using a curvature surface that provides mounting stability despite the angle of attachment.

Still another objective of this invention is to provide a anchoring base and rod clamp system that permits the use of a single support rod.

Other objects and advantages of this invention will become apparent from the following description taken in conjunction with the accompanying drawings wherein set forth, by way of illustration and example, certain embodiments of this invention. The drawings constitute a part of this specification and include exemplary embodiments of the instant invention and illustrate various objects and features thereof.

DETAILED DESCRIPTION OF THE PREFERRED EMBODIMENT

As required, detailed embodiments of the present invention are disclosed herein, however, it is to be understood that the disclosed embodiments are merely exemplary of the invention which may be embodied in various forms. Therefore, specific functional and structural details disclosed herein are not to be interpreted as limiting, but merely as a basis for the claims and as a representative basis for teaching one skilled in the art to variously employ the present invention in virtually any appropriately detailed structure.

Figure 1:
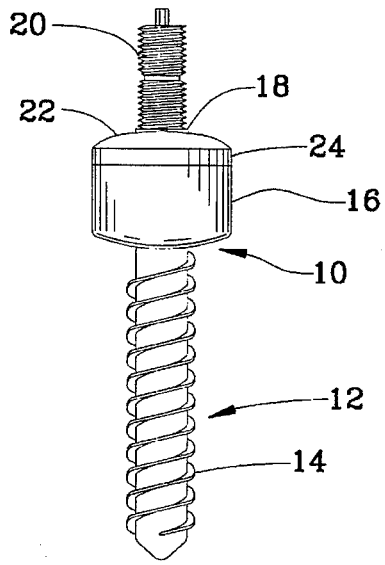
FIG. 1 is a side view of the articulating toggle bolt bone screw of the instant invention.

Now referring to FIG. 1, the articulating toggle bolt bone screw 10 of the instant invention is defined by an anchoring base 12 formed from stainless steel, titanium, thermoplastic, composite, bovine, coral, POLYSORB, or the like rigid material. The anchoring base provides fixed placement in bone structure by use of a threaded shaft 14 having a coarse self-taping thread disposed along a length thereof. An upper portion of the anchoring base 12 forms a spherical shaped receptacle socket 16 to engage the foundation 18 of a toggle bolt shaft 20 can also be formed from the aforementioned rigid materials. The toggle bolt 20 provides a predetermined range of rotation in conjunction with a centrally disposed aperture 22 found on attachment cap 24. Machine or english threads along the length of the bolt extend outwardly from the cap 24 for use in securing various components to the bolt and permanent attachment thereafter when a locking nut is installed. As depicted in the drawings, bolt 20 may include a notch along the length thereof allowing the bolt to be broken off at a predetermined position once installed so as to reduce the profile of implantation.

It is noted that the apparatus can be formed from various thermoplastic polyamides such as nylon. In addition to the commonly known advantages of plastic, the material provides the surgeon with the ability to customize a bone screw installation. For instance, if the spinal reconstruction requires an offset angular attachment with an unusually large extension, the use of an oversized plastic toggle bolt will allow the surgeon to insert spacers, cross connects, or rod attachment, not shown, to conform to an individual patient's requirement. Once installed, the surgeon can easily cut the remaining portion of the toggle bolt that is not necessary.

Figure 2:
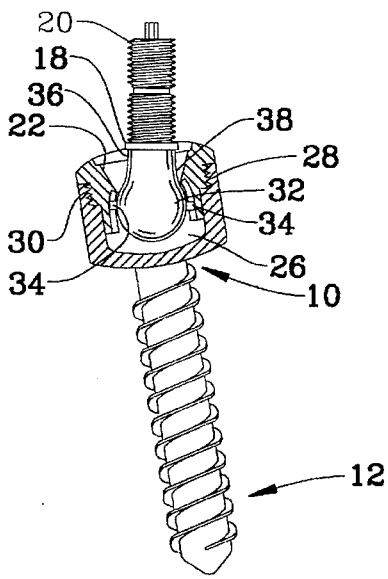
FIG. 2 is a cross sectional side view of the bone screw with the toggle bolt shown in an offset position.
Figure 2:
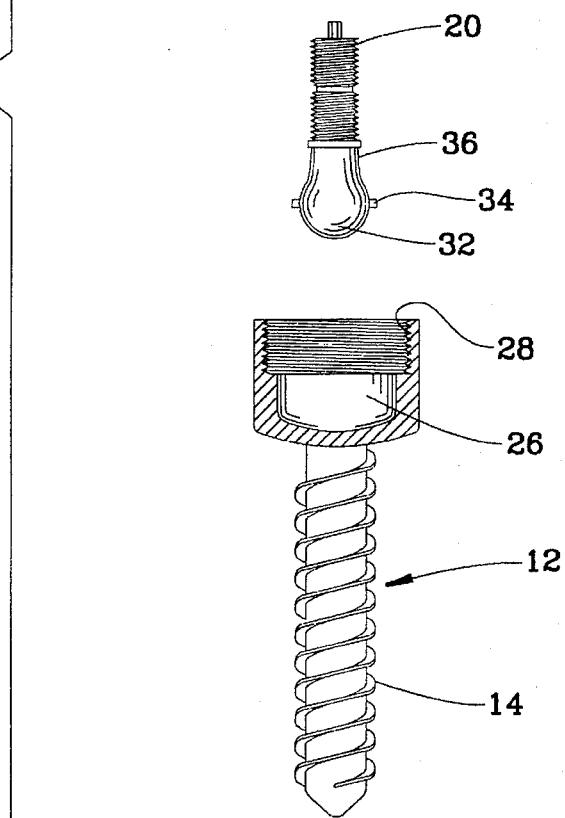

FIG. 2 sets forth a cross sectional side view of the bone screw 10 clearly depicting the spherical socket chamber 26. The chamber 26 is defined by a cup shaped opening having an internal thread 28 engaging the external thread 30 on the attachment cap 24. The socket 16 and attachment cap 24 form a ball shaped chamber allowing the rotational movement of a ball shaped end 32 of toggle bolt base 18. Tabs 34 are positioned on either side of end 32 to prevent spinning within the chamber by engagement of diametrically opposed slots that run both perpendicular and vertical providing a slidable point of rotation. Median which provides transition between shaft 20 and end 32 is operatively associated with the aperture 22 setting forth a diameter smaller than the diameter of the bolt end 32. The median 36 has a curved surface that engages the side wall of aperture 22 providing up to twenty five degrees of motion-range over a 360 degree pattern from a longitudinal axis defined along the length of said shank 14. The inner edge of aperture 22 is sized to prevent passage of end 32. In addition, a preferred embodiment of the invention allows deformation of the aperture edge 38 during engagement of the toggle bolt 20 so as to permanently wedge the end 32 and inner edge 38 together to prevent any rotation or angular movement once the surgeon has determined the optimum fixation position. Permanent positioning can be enhanced by use of roughened surfaces such as shot blasted or striated surfaces. Further, material selection or construction of wedge shaped ball tabs which allow deformation concomitantly with the aperture inner edge 38 permit additional fixation.

Figure 3:
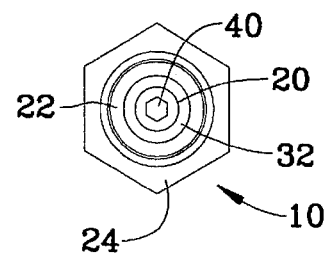
FIG. 3 is a top view of a hex shaped embodiment of the bone screw.
Figure 6:
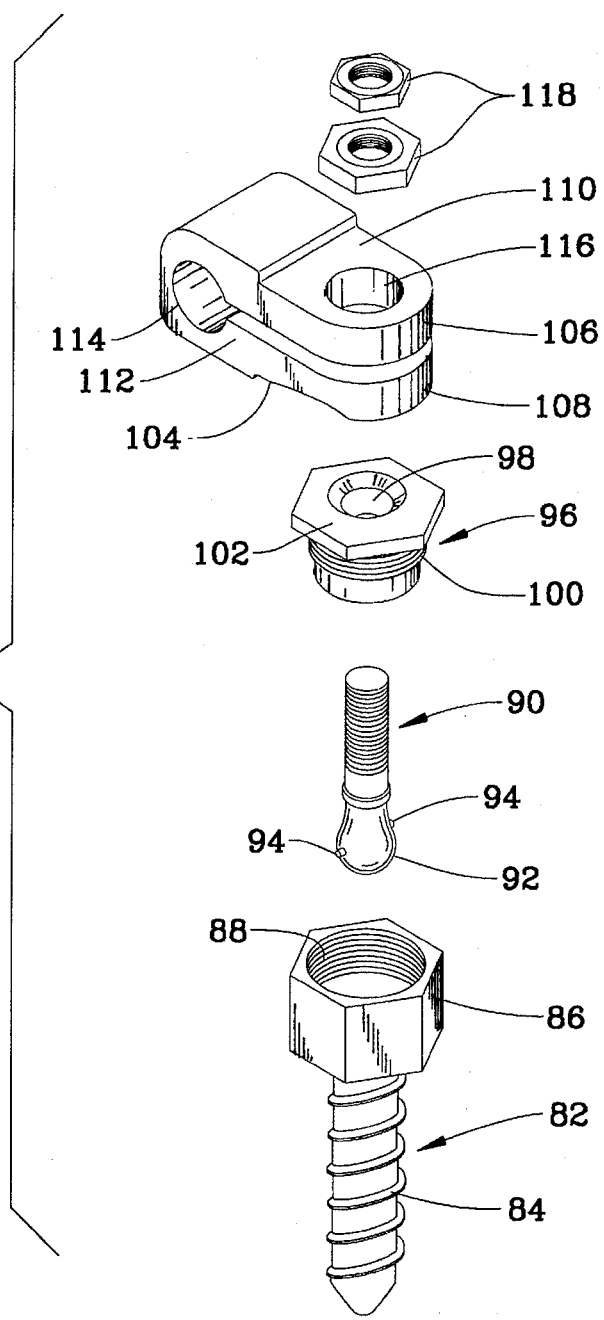
FIG. 6 is an exploded perspective view of the hex shaped embodiment of the bone screw with rod clamp.

FIG. 3 is a top view of the bone screw 10 illustrating the attachment cap 24 having centrally disposed aperture 22. Toggle bolt 20 can be angled by rotation of the shaft within the confines of the aperture. Tabs 34 engage slots within the side wall of the chamber allowing a pivot and slid movement of the bolt. The anchoring base and attachment cap can be made in the form of a conventional hex head allowing ease of installation, see FIG. 6, or use a round body. In either embodiment, it has been found that forming a hex head 40 on the end of the bolt 20 facilitates attachment, holding, or removal by use of a conventional torque wrench.

Figure 4:
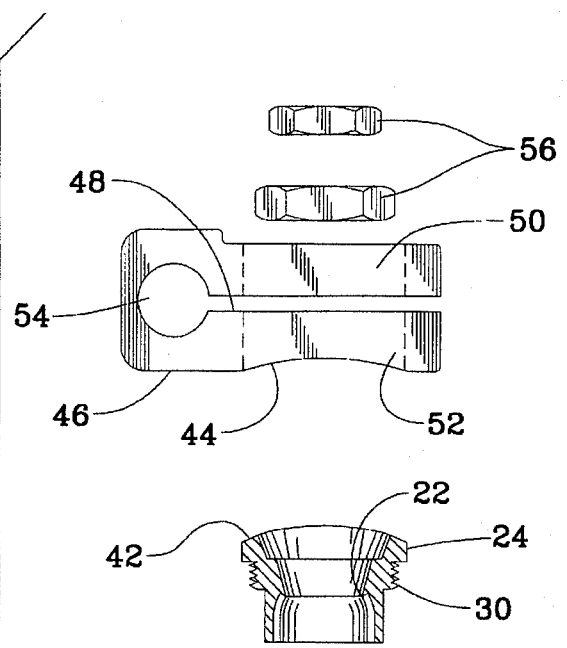
FIG. 4 is an exploded view of the bone screw with rod clamp.

Now referring to FIG. 4, an exploded view of the articulating toggle bolt bone screw sets forth the anchoring base 12 with threaded shaft 14 and the spherical socket chamber 26 with internal thread 28. Threaded toggle bolt base 12 has ball shaped end 32 with tabs 34 to prevent spinning of the bolt in socket 26. The median 36 clearly shows an hourglass shape operatively associated with the aperture 22 of attachment cap 24. External threads 30 of cap 24 provide engagement with anchoring base 12. It should be obvious to one skilled in the art that low profile applications can be obtained by various cap attachment methods including welding or press fit, not shown, but within the scope of the instant invention. The upper surface 42 of the cap 24 is rounded, i.e. convex, for engaging the lower surface 44 of a rod clamp 46. Rod clamp 46 is formed from a bifurcated compressible sleeve having a longitudinal slot with an aperture 54 disposed perpendicular thereto for insertion of rod supports. A spaced apart upper section 50 and lower section 52 provides an area for compression by removal of said slot 48 allowing the clasping of a rod placed in aperture 54. In operation, rod clamp 46 is coupled to the toggle bolt 20 by the use of a conventional locking nuts 56 shown in duplicate as the preferred method of preventing unintentional loosening. The rod aperture 54 permits coupling to a conventional support rod, not shown, wherein tightening of the nuts 56 to the bolt 20 causes compression of the rod aperture 54 When the upper section 50 and lower section 52 are forced together. The lower section 52 has a curvature 44 to allow broad surface area contact with the upper surface 42 of the cap 24 throughout the range of angular bolt motion. To increase support of the rod and attachment to the bolt 20, the surface of the aperture 54 and joining surfaces 44 and 42 can be knurled or otherwise roughened providing a texture for increased gripping ability. As previously noted, it is deemed within the scope of this invention to use spacers between attachment cap 24 and rod clamp 46 as well as variations of the clamping mechanism for attachment to devices such as cross links and the like ancillary devices.

Figure 5:
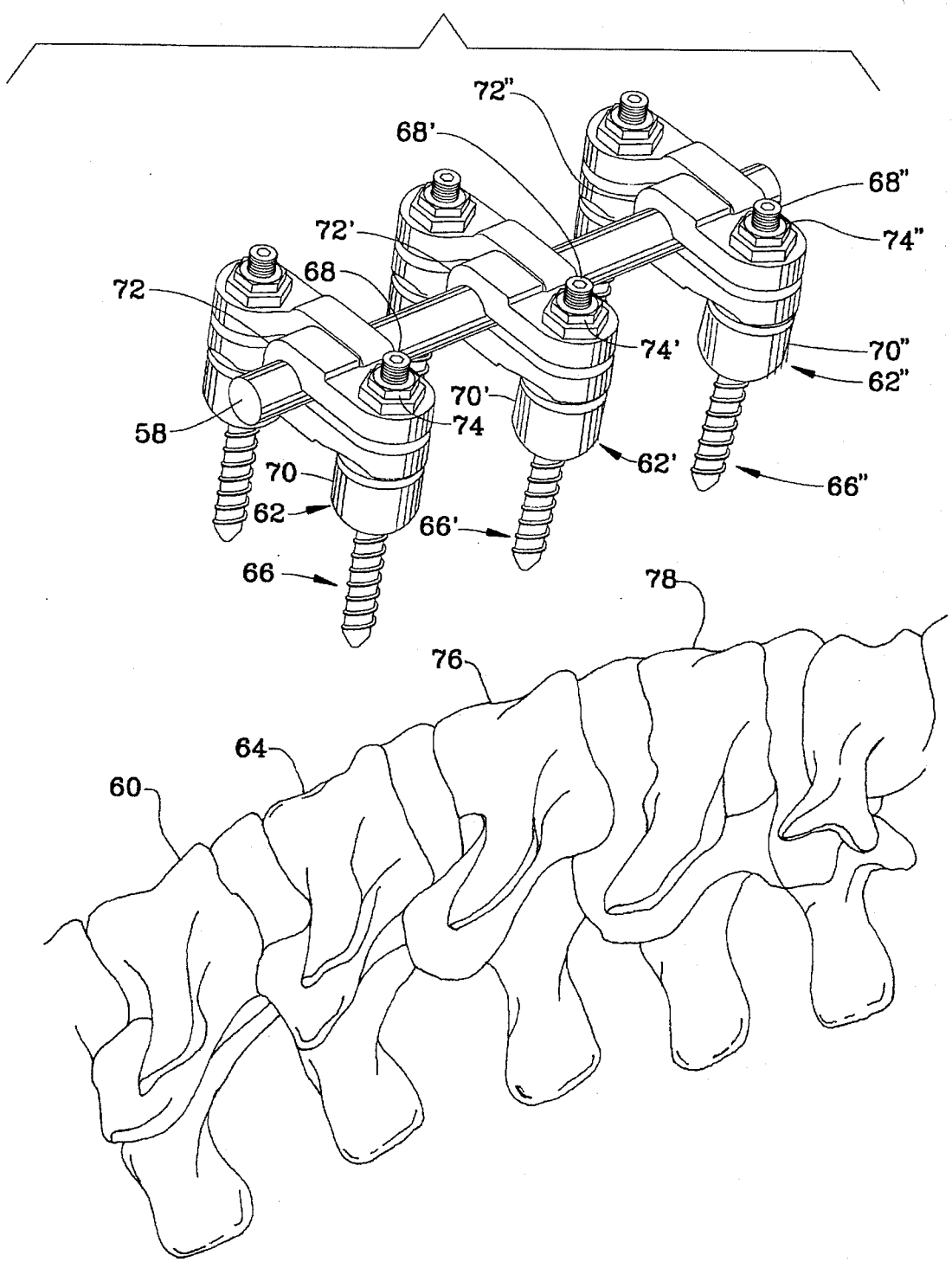
FIG. 5 is a perspective view of a spinal implant illustrating the angular adjustment of individual bone screws and setting forth an alternative embodiment using half size rod clamps for a single support rod system.

FIG. 5 sets forth a pictorial view of the bone screws ready for attachment to a spine. In this example, support rod 58 is shown in a straight axis over a parallel plane to the longitudinal axis of spine 60. Screw 62 to be threaded into the bone 64 perpendicular to the support rod. As previously described the screw 62 utilizes the threaded shaft 66 for attachment to bone. The toggle bolt 68 is positioned within the socket 70 and projects through the cap aperture for attachment to alternative embodiment clamp 72 which frictionally engages the support rod 58 by use of the locking nuts 74. Mirror image anchoring screws and rod clamps are depicted but not numbered so as to provide drawing clarity. In this particular embodiment, the rod clamp 72 has a reduced area of attachment to the rod 58 providing a singular rod implant system. Unique to this invention is the ability to use a single support rod yet find proper pedicle anchoring. Screw 62' is threaded into the bone 76 at approximately a seven degree angle to the support rod 58. The screw 62' utilizes the threaded shaft 66' for attachment to the bone wherein toggle bolt 68' is positioned within the socket 70 and slightly offset for which the cap and clamp surface provide a compensating surface area for attachment. Alternative embodiment clamp 72' is then engaged to the support rod 56 by use of the locking nuts 74'. Screw 62" threaded into the bone 78 at approximately a fifteen degree angle to the support rod 56. The screw 62" utilizes the threaded shaft 66" for attachment to the bone wherein toggle bolt 68" is positioned within the socket 70" and slightly offset for which the cap and clamp surface compensate. Alternative rod clamp 72" is then engaged to the support rod 56 by use of the locking nuts 74". Now referring to FIG. 6, an exploded perspective view of the articulating toggle bone screw of the preferred embodiment sets forth the anchoring base 82 with threaded shaft 84 and the hex shaped socket chamber 86 with internal thread 88. The hex shaped housing allows the use of leverage tools for insertion of the anchoring base 82 in strong bone structure. Threaded toggle bolt base 90 has ball shaped end 92 with tab 94 to help prevent spinning of the bolt 90 in socket 86. Attachment cap 96 is shown with aperture 98 using external threads 100 for engagement with threads 88 anchoring base 86. As with the rounded body embodiment, the upper surface 102 of the cap is made available for engaging the lower surface 104 of conventional implant devices such as rod clamp 106. The rod clamp 106 is formed from a bifurcated compressible sleeve having a longitudinal slot 108 defined by a spaced apart upper section 110 and lower section 112 with an aperture 114 disposed perpendicular thereto. The rod clamp 106 is coupled to the toggle bolt 90 by insertion of the bolt 90 through bolt hole 116 for coupling to conventional locking nuts 118 shown in duplicate as the preferred method of preventing unintentional loosening.

It is to be understood that while we have illustrated and described certain forms of our invention, it is not to be limited to the specific forms or arrangement of components herein described and shown. It will be apparent to those skilled in the art that various changes may be made without departing from the scope of the invention and the invention is not to be considered limited to what is shown in the drawings and described in the specification.

What is claimed is:

1. An articulating toggle bolt bone screw for surgical implantation comprising:

an anchoring base having a rigid shank with a self-taping threaded first end for securing into human bone and a cylindrical shaped second end having an enlarged sidewall forming a socket;

a bolt constructed of rigid material having a first spherically shaped end insertable into said socket and a threaded second end receptive to a locking nut;

and an attachment cap frictionally engaging an inner surface of said enlarged sidewall of said anchoring base forming a receptacle for holding said first end of said bold in a fixed position relative to said anchoring base, said attachment cap having a rounded upper inner surface and a centrally disposed sized aperture allowing said second end of said bolt to articulate over a predetermined range of motion;

whereby said anchoring base is threaded into human bone wherein said second end of said bolt is available for attachment to conventional implant component devices, wherein tightening of a locking nut to said second end of said bolt frictionally engages said first spherically shaped end against said inner surface of said attachment cap securing said bolt in position.

2. The attachment screw according to claim 1 wherein means for securing is further defined as an attachment cap engagable with said anchoring base forming a receptacle for holding said first end of said bolt in a fixed position relative to said anchoring base, said attachment cap having a sized aperture allowing said range of motion.

3. The attachment screw according to claim 1 wherein said attachment cap includes a curved upper surface.

4. The attachment screw according to claim 1 wherein range of motion is approximately twenty five degrees throughout a 360 degree pattern from a longitudinal axis defined along the length of said shank.

5. The attachment screw according to claim 1 wherein said bolt includes at least one tab extending outwardly from a surface of said spherically shaped first end to prevent circular rotation about an axis formed along a length of said bolt.

6. The attachment screw according to claim 1 wherein said anchoring base and bolt are constructed from steel.

7. The attachment screw according to claim 1 wherein said anchoring base and bolt are constructed from plastic.

8. The attachment screw according to claim 1 wherein said second end of said anchoring base and said means for securing have a symmetrical hex shaped diameter.

9. The attachment screw according to claim 1 wherein said first end of said bolt including a tab extending outwardly from a surface of said spherically shaped first end for wedging said bolt in a fixed position relative to said anchoring base.

10. A surgically implantable rod attachment apparatus comprising: an anchoring base constructed from a steel shank having a single longitudinal axis with a first end forming a self-taping thread available for insertion into bone and a second end having an enlarged sidewall forming a first spherical shaped socket; a bolt constructed from a single piece of rigid material having a single longitudinal axis with a first spherically shaped end insertable into said socket and a threaded second end receptive to a locking nut; an attachment cap nut frictionally engaging an inner surface of said enlarged sidewall of said anchoring base forming a receptacle for holding said first end of said bolt in a fixed position relative to said anchoring base, said attachment cap having a rounded upper inner and outer surface and a centrally disposed sized aperture allowing said bolt to articulate over a predetermined range of motion; a bifurcated compressible sleeve having a spaced apart upper section and lower section forming a longitudinal slot with an aperture disposed perpendicular thereto, said aperture available for insertion of a conventional support rod, said lower section having a concave surface for frictional engagement of said upper surface of said attachment cap; and at least one lock nut engagable with said threaded second end of said bolt for securing said rod clamp to said bolt;

whereby said anchoring base is securable to rigid bone structure by threading said anchoring base into bone structure wherein said bolt is available for angular rotation within said aperture for proper positioning of said clamp having a support rod placed through said clamp aperture allowing securement to said anchoring base by tightening said lock nut frictionally engaging said first end of said bolt to said inner surface of said attachment cap.

11. The implantable attachment according to claim 10 wherein said attachment cap is threaded to said anchoring base.

12. The implantable attachment according to claim 10 wherein said attachment cap is welded to said anchoring base.

13. The implantable attachment according to claim 10 wherein said attachment cap is press fit to said anchoring base.

* * * * *

UNITED STATES PATENT AND TRADEMARK OFFICE
CERTIFICATE OF CORRECTION

PATENT NO. : 5,628,740
DATED : May 13, 1997
INVENTOR(S) : Thomas S. Mullane

It is certified that error appears in the above-indentified patent and that said Letters Patent is hereby corrected as shown below:

On the title page: Item 63, change
"Continuation of Ser. No. 173,619, Dec, 23, 1995, abandoned." to --Continuation of Ser. No. 173,619, Dec. 23, 1993, abandoned.--

Signed and Sealed this

Sixteenth Day of September, 1997

Attest:

BRUCE LEHMAN

*Attesting Officer*     *Commissioner of Patents and Trademarks*